United States Patent [19]
Dalla Betta et al.

[11] Patent Number: 5,486,336
[45] Date of Patent: Jan. 23, 1996

[54] NOX SENSOR ASSEMBLY

[75] Inventors: Ralph A. Dalla Betta, Mountain View, Calif.; Daniel L. Reed, Boulder, Colo.; Priscilla Schubert, Pacifica, Calif.

[73] Assignee: Catalytica, Inc., Mountain View, Calif.

[21] Appl. No.: 80,679

[22] Filed: Jun. 22, 1993

Related U.S. Application Data

[63] Continuation of Ser. No. 536,888, Jun. 12, 1990, abandoned.

[51] Int. Cl.$^6$ .................................................. G01N 25/20
[52] U.S. Cl. .............................. 422/90; 422/95; 422/98; 60/276
[58] Field of Search .................................. 338/34; 60/276, 60/295, 301; 423/235, 236, 239.1; 422/83, 95, 88, 90, 98, 174, 180; 436/106, 109–110, 116–118, 147, 151, 159

[56] References Cited

U.S. PATENT DOCUMENTS

| | | |
|---|---|---|
| 2,751,281 | 6/1956 | Cohn. |
| 3,167,947 | 2/1965 | Crawford .............................. 73/25.01 |
| 3,460,909 | 8/1969 | Gayle. |
| 3,476,517 | 11/1969 | Smith. |
| 3,488,155 | 1/1970 | Ayers. |
| 3,522,010 | 7/1970 | Archer. |
| 3,537,823 | 11/1970 | Innes. |
| 3,540,851 | 11/1970 | Vree et al.. |
| 3,547,587 | 12/1970 | Innes. |
| 3,586,486 | 6/1971 | Kim et al.. |
| 3,599,427 | 8/1971 | Jones et al.. |
| 3,607,084 | 9/1971 | Mackey et al.. |
| 3,791,936 | 2/1974 | Pebler et al.. |
| 3,906,721 | 12/1975 | Michell et al.. |
| 3,967,933 | 7/1976 | Etess et al.. |

(List continued on next page.)

FOREIGN PATENT DOCUMENTS

| | | |
|---|---|---|
| 0257842 | 3/1987 | European Pat. Off.. |
| 3728331 | 3/1989 | Germany. |
| 58-719785 | 6/1983 | Japan. |
| 2066963 | 7/1981 | United Kingdom. |
| WO88/05911 | 8/1988 | WIPO. |

OTHER PUBLICATIONS

Arai et al. "Opt. Detect. Nit. Mon. Metal Porphine...Film", *Chem. Letters,* the Chem. Soc. Japan, pp. 521–524, (1988).

"Removal of Nitric Oxide from Exhaust Gas with Cyanuric Acid" Siebers et al. *Combustion and Flame* 79:31–46 (1990).

"Model for a Temperature Dependence . . . by $NH_3$ Fresh Catalyst" Nam et al. *Ind. Eng. Chem. Prod. Res. and Devel.,* (1986)25:186–192.

"Cyanuric Acid . . . and the effects of Oxygen" Wickie et al., *Combustion and Flame,* 78: 249–255 (1989).

"The activity of supported vanadium . . . the selective reduction of NO with ammonia" by Bosch et al. *Applied Catalysis* 29:239–248 (1986).

"Lithium–Vanadium Bronzes . . . Selective Reduction of Nitric Oxide". *Catalysis Today* 4:139–154 (1989).

"Catalytic Reduction . . . on Vanadium Oxide and Iron–Chromium Oxide" *Ind. Eng. Chem. Prod. Res. Devel.,* 14:268–273 (1975).

*Primary Examiner*—Jeffrey R. Snay
*Attorney, Agent, or Firm*—Morrison & Foerster

[57] ABSTRACT

This invention is a self-contained $NO_x$ sensor assembly. It may be used to detect $NO_x$ levels in a flowing gas stream such as might be found in an exhaust gas from a combustion process and to produce a measurable electrical output related to the content of $NO_x$ measured. The $NO_x$ sensor assembly is of a configuration that may be detached from a mounting and replaced. The sensor assembly comprises two sensor elements one of which is made up of a catalyst on a temperature measuring device. The other is a gas stream ambient temperature measuring device. The catalyst is selected and configured so that it selectively reduces $NO_x$ and the resulting heat of the reaction raises the temperature of the allied temperature measuring device. The sensor assembly also contains a $NO_x$ reductant source. The sensor assembly may be placed in a moving vehicle for measuring $NO_x$ levels in its exhaust gas.

18 Claims, 2 Drawing Sheets

U.S. PATENT DOCUMENTS

| | | | |
|---|---|---|---|
| 4,001,756 | 1/1977 | Heijne | 422/98 |
| 4,005,001 | 1/1977 | Pebler. | |
| 4,029,472 | 6/1977 | Michell et al.. | |
| 4,063,898 | 12/1977 | Fisher. | |
| 4,115,067 | 9/1978 | Lyshkow. | |
| 4,129,848 | 12/1978 | Frank et al.. | |
| 4,169,126 | 9/1979 | Iles | 422/98 |
| 4,170,455 | 10/1979 | Henrie | 422/98 |
| 4,188,190 | 2/1980 | Muraki et al.. | |
| 4,236,895 | 12/1980 | Stahl. | |
| 4,257,777 | 3/1981 | Dymond et al.. | |
| 4,298,574 | 11/1981 | Bohl. | |
| 4,305,724 | 12/1981 | Micko. | |
| 4,315,753 | 2/1982 | Bruckenstein et al.. | |
| 4,325,912 | 4/1982 | Sawa et al.. | |
| 4,343,768 | 8/1982 | Kimura. | |
| 4,355,056 | 10/1982 | Dalla Betta et al.. | |
| 4,473,536 | 9/1984 | Carberg et al.. | |
| 4,532,492 | 6/1985 | Esper et al. | 422/98 |
| 4,647,777 | 3/1987 | Meyer. | |
| 4,731,221 | 3/1988 | Perry. | |
| 4,731,226 | 3/1988 | Takahata et al. | 422/98 |
| 4,778,764 | 10/1988 | Fine. | |
| 4,822,564 | 4/1989 | Howard. | |
| 4,836,012 | 6/1989 | Doty et al.. | |
| 4,840,913 | 6/1989 | Logothetis et al.. | |
| 4,861,567 | 8/1989 | Heap et al. | 423/239 |
| 4,886,650 | 12/1989 | Perry | 423/239 |
| 4,957,705 | 9/1990 | Uchikawa | 422/98 |
| 5,171,558 | 12/1992 | Gardner-Chavis et al. | 423/239.1 |

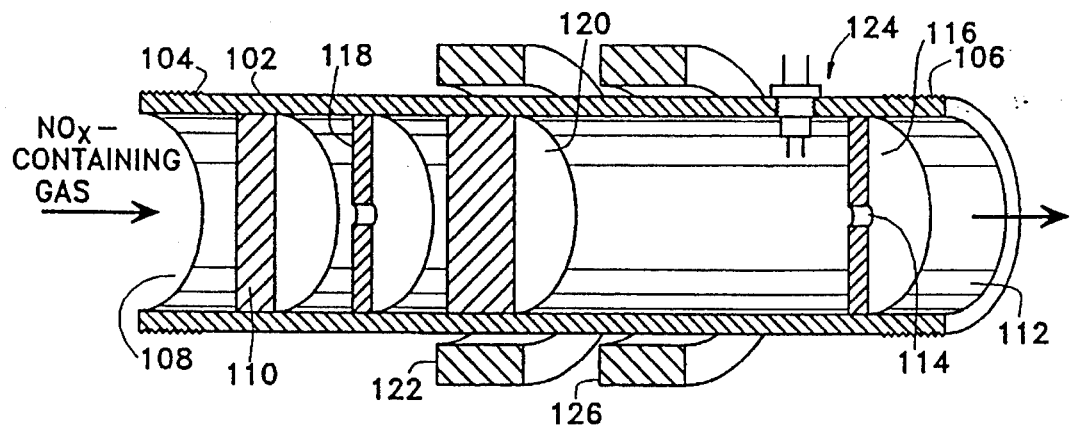
Figure 3-A
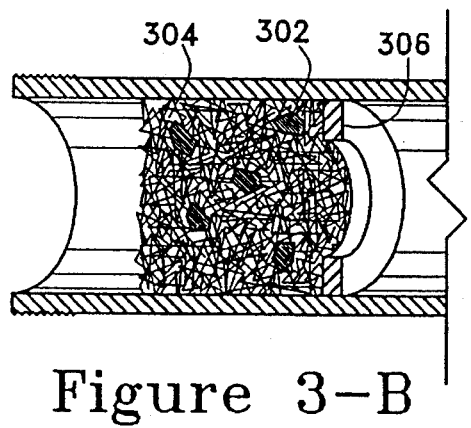
Figure 3-B
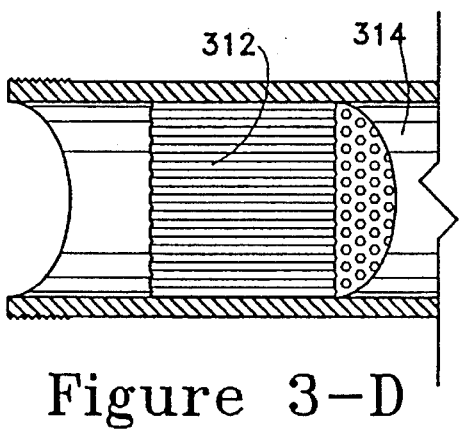
Figure 3-D
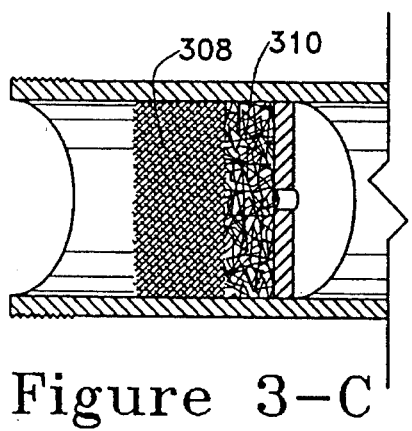
Figure 3-C
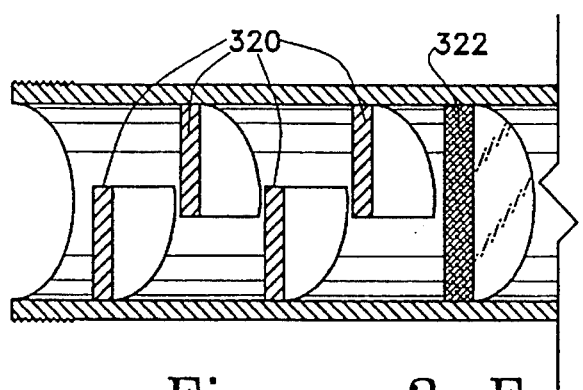
Figure 3-E

NOX SENSOR ASSEMBLY

This application is a continuation of application Ser. No. 07/536,888, filed Jun. 12, 1990, now abandoned.

FIELD OF THE INVENTION

This invention is a self-contained $NO_x$ sensor assembly. It may be used to detect $NO_x$ levels in a flowing gas stream such as might be found in an exhaust gas from a combustion process and to produce a measurable electrical output relative to the content of $NO_x$ measured. The $NO_x$ sensor assembly is of a configuration that may be mounted in motor vehicles and other mobile locations, requires low power, and no additional chemical reagents.

The sensor assembly comprises two sensor elements one of which is made up of a catalyst on a temperature measuring device. The other is a gas stream ambient temperature measuring device. The catalyst is selected and configured so that it selectively reduces $NO_x$ and the resulting heat of reaction raises the temperature of the allied temperature measuring device. The sensor assembly also contains a reductant source.

The sensor assembly may be placed in a moving vehicle for measuring $NO_x$ levels in its exhaust gas.

BACKGROUND OF THE INVENTION

Exhaust gases produced by burning fuels using air as the source of oxygen typically contain small but significant amounts of various nitrogen oxides (NO, $NO_2$, $N_2O_3$, etc.) collectively and interchangeably known as $NO_x$. $NO_x$ is often present in these exhaust gases whether the source is a stationary source such as a boiler or is mobile such as an automobile or truck. Although small, the $NO_x$ content is a necessary and, therefore, undesirable participant in the photochemical reaction creating modern "smog".

There are a number of ways in which the $NO_x$ may be removed or treated or even its initial synthesis prevented; however, each such process strongly benefits from use of an accurate monitor for detecting low levels of $NO_x$. The detector may be used in a variety of processes to reduce the amount of $NO_x$ the process produces such as by:

1. converting $NO_x$ to $N_2$ by reaction with a reductant such as $NH_3$ where the reductant addition rate is controlled by the level of $NO_x$ found in the stream to be treated, 2. controlling the rate of exhaust gas recirculation ("EGR") to lower flame temperature and, therefore, the $NO_x$ level, and 3. adjusting boiler burner operations, including dilution air flow, to control $NO_x$ production levels.

There are, however, few low level $NO_x$ sensors available which are practically suitable for inclusion in closed loop controllers or for mobile use. Major problems found in the prior measurement devices have included the lack of sensitivity and toughness. An ability to measure low levels of $NO_x$ in mobile source combustion gases is desireable.

There are a number of methods known for detecting $NO_x$ in flowing gas streams. Perhaps the most well-known of the processes currently used involves instruments using the chemiluminescent reaction of nitric oxide and ozone. The accuracy of many $NO_x$ sensors, including chemiluminescent sensors, suffers because of interference from other gases which may be found in a combustion gas stream, e.g., $SO_2$, CO, $H_2$, $H_2O$, and various hydrocarbons. Additionally, ozone is highly reactive and often raises reactivity problems with analyzer components, e.g., O-rings, metals used in the analyzer, and the like. The process operates by the reaction of injected ozone and the nitric oxide in a sample within a reaction chamber having a transmissive window through which the light produced by the chemiluminescent reaction is monitored by a detector. The window in the reaction chamber must be kept scrupulously clean to maintain analyzer sensitivity and calibration. Water causes substantial problems in these devices. Typical apparatus using this process may be found in U.S. Pat. Nos. 3,967,933 to Etess et al.; 4,236,895 to Stahl; 4,257,777 to Dymond; 4,315,753 to Bruckenstein et al.; and 4,822,564 to Howard. The use of a chemiluminescent nitrogen oxide monitoring device in controlling a nitrogen oxide removal unit placed on the outlet of a boiler is shown in U.S. Pat. No. 4,188,190 to Muraki et al. The devices disclosed herein could be substituted for the nitrogen oxide sensors shown in the Muraki et al. Because of the sensitivity of the optical portions of the devices to vibration, and due to the size and cast of these devices, the use of chemiluminescent analyzers is wholly unsuitable for mobile source $NO_x$ sensors.

Another procedure involves the use of an infrared beam, detector, and a comparator chamber. In U.S. Pat. No. 4,647,777 to Meyer, a beam of infrared light is passed through a gas sample and into a selective infrared detector. The beam is split and one portion passes through a chamber containing a fluid which absorbs the spectral wavelengths of the selected gas. The two beams are compared and the difference between the two beams gives an indication of the amount of selected gas in the sample. Although such instruments can measure NO and $NO_x$, they suffer from the same shortcomings as do the chemiluminescent analyzers: clean optical surfaces are required, significant sample pretreatment is required, and the instrument has significant maintenance requirements.

U.S. Pat. No. 4,836,012 to Doty et al. shows a semiconductor device made up of a photovoltage cell which, upon exposure to light, develops a voltage or current which varies as a function of the type of gas sorbed. The device requires a "thin light-transmitting gas-absorbing metal Schottkey layer having electrical properties which vary with the type of gas sorbed". Detection of CO, hydrocarbon, water vapor, etc., is suggested; detection of NO is not.

Other methods of determining the trace amounts of $NO_x$ which may be present in a gas stream are known. For instance, U.S. Pat. No. 3,540,851 to Vree et al. suggests a process in which a gaseous mixture containing substituents such as carbon oxides, nitrogen oxides, sulfur oxides, and oxygen is separated into two streams. One stream is desirably mixed with a ballast gas and sent into a reference arm of a measuring apparatus; a second stream is passed after mixing both with nitrogen and a carrier gas, such as helium, and subjected to an electric discharge. The thus treated gases are passed through a conventional electrometer. The excited $NO_x$ passes to an ionic state and gives off a measurable electron.

U.S. Pat. No. 4,115,067 to Lyshkow suggests a process for using a substrate which is sensitive to the pollutant to be measured and monitoring the change in color or reflectivity of the sensitized substrate. Lyshkow suggests the use of a substrate upon which silica which has been impregnated with a mixture of sulfanilic acid and N-(1-naphthyl)-ethylenediamine dihydrochloride. The mixture reacts with $NO_2$, changes the color of the substrate, and decreases the reflectivity of the substrate having the silica gel coating. Lyshkow suggests that the treated substrate be contacted with the gas to be measured and moved at a constant rate past a device which measures the change of reflectivity of the surface. In this way the amount of $NO_2$ is measured.

The U.S. Pat. No. 4,778,764 to Fine describes a device and a process in which a sample is injected with a solvent into a liquid chromatographic column to separate the various materials present in the sample. The output of the column is then burned in the presence of a variety of detectors for one or more of $NO_x$, $SO_2$, $CO_2$, and halogens.

U.S. Pat. No. 4,840,913 to Logothetis et al. suggests a method for sensing nitrogen oxides, particularly in the exhaust flow of an internal combustion engine. The gas is passed through an oxidation catalyst which is formed over an oxide sensor. The oxidation catalyst is intended to oxidize all reducing species ($CO$, $H_2$, hydrocarbons, alcohols, etc.) which are carried in the gas to be measured. Nitrogen monoxide is oxidized to $NO_2$ as well. The oxidized gas passes to an oxide sensor such as a $SnO_2$ or $ZnO$.

U.S. Pat. No. 4,473,536 to Carberg et al. suggests a process for controlling a $NO_x$ reduction process using a nonspecific $NO_x$ sensor.

None of the above disclosures suggest a process or an apparatus in which a catalytic element is used to detect the presence of a gaseous component. Because of their complexity, none are suitable for use in mobile $NO_x$ sources such as automotive spark ignition or diesel engines.

The concept of using the temperature rise of a gas as it passes through a catalyst bed as an indicator of the content of a component of that gaseous mixture has been shown. For instance, in U.S. Pat. No. 2,751,281 to Cohen, a method is taught for measuring low concentrations of gas impurities, such as oxygen, in the range of 0.0001% to 0.001%. A thermocouple is placed such that a cold junction is on the upstream side of a bed of catalyst and the hot junction is placed on the downstream side of that bed. As the gas flows across the catalyst, the temperature of the gas rises and is detected and the impurity content of the incoming gas is calculated. U.S. Pat. No. 3,488,155 to Ayers shows a similar process in which the temperature on each side of a hydrogenation catalyst bed is measured during the flow of a gas containing hydrogen. The temperature difference is related to the hydrogen content of the incoming gas stream.

The U.S. Pat. No. 3,537,823 to Ines suggests a process for measuring the quantity of "smog forming hydrocarbons in a gas sample" by measuring the temperature rise in an oxidation catalyst bed. Moreover, a related process is found in U.S. Pat. No. 3,547,587 also to Ines.

U.S. Pat. No. 3,607,084 to Mackey et al. teaches a process for the measurement of a combustible gas content by locating a pair of wires in a small chamber containing a volume of gas with combustibles therein. One wire is coated with a catalytic mixture of a metal oxide and a powdered metal of the platinum group and the other is apparently uncoated. Electrical power supplies heat to both wires. The difference in resistance caused by the change in temperature of the wire coated with the catalytic mixture provides an indicator of the amount of combustibles in that gas chamber.

U.S. Pat. No. 4,170,455 to Henrie also suggests a method for the monitoring of the hydrogen or oxygen content of a gas stream by measuring the temperature upstream and downstream of an oxidation catalyst. U.S. Pat. No. 4,343,768 to Kimura shows a gas detector formed using semiconductor technology. The detector uses dual heating elements over a channel adapted for gas flow. One of the heating elements is coated with a "catalytic or gas responsive film" which may be platinum or palladium. The increase in the temperature of the catalytic film is detected in terms of the variation in electrical resistance in the content of the gas stream calculated.

Finally, U.S. Pat. No. 4,355,056 to Dalla Betta et al. suggests a differential thermocouple combustible sensor in which one junction of the thermocouple is catalytically coated and the other junction is not. The gas stream contains such gases as carbon monoxide and hydrogen and the sensor is said to be "insensitive to contaminants such as $SO_2$ and NO".

None of these disclosures teaches a self-contained $NO_x$ sensor assembly containing a $NO_x$ reductant source and a catalytic $NO_x$ detector which is suitable for placement in a moving vehicle where size, weight, power requirements, and cost are important factors.

BRIEF DESCRIPTION OF THE DRAWINGS

FIGS. 3A-3E show a number of variations of the inventive device.

SUMMARY OF THE INVENTION

Figure 1:
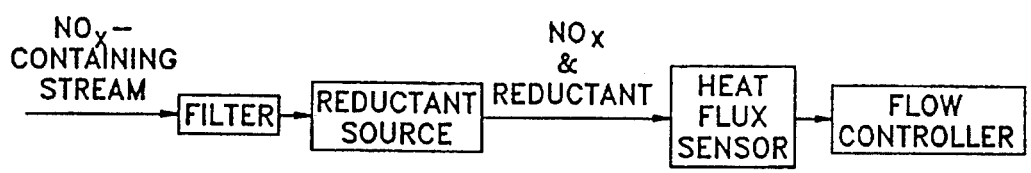
FIG. 1 is a block diagram of this inventive device.

As was noted above, the invention is a self-contained $NO_x$ sensor assembly suitable for measuring $NO_x$ in a flowing gas stream such as might be found as the exhaust of an internal combustion engine burning diesel or gasoline type fuels.

The self-contained $NO_x$ sensor assembly is made up of a housing which contains the rest of the elements, a $NO_x$ reductant source, and heat flux detector to detect the reaction between the $NO_x$ and the $NO_x$ reductant. The $NO_x$ sensor assembly desirably also contains a flow controlling device such as an orifice to control the flow rate of gas to be measured through the $NO_x$ sensor assembly and heaters to control the temperature of the $NO_x$ reductant source and the catalytic sensor element. Other elements may include filters for remaining particulate matter, connectors for measurable output, baffles for shielding the heat flux assembly, etc.

The heat flux detector may be made up of two major discrete functional portions: a catalytic sensor element and a reference sensor element. The catalytic element has on its outside periphery a catalyst; in thermal contact is a temperature measuring device. Both are generally thermally isolated from the operating environment and each other. The catalyst is selected and merged with the temperature measuring device so that the $NO_x$ in the flowing gas stream is selectively reduced to $N_2$ and $H_2O$ on the catalyst surface using an added $NO_x$ reductant. The $NO_x$ reductant is supplied by the $NO_x$ reductant source. The temperature measuring device may be well-known devices such as resistance-temperature-detectors (RTD), thermistors, or thermocouples which detect the small temperature rise occurring due to the $NO_x$ reduction reaction taking place on the catalyst. The catalyst and temperature measuring device should be in close (ideally, contiguous) physical proximity and constructed in such a way that they retain most of the heat of reaction produced by the reduction reaction. The heat of reaction should then cause only the temperature of the temperature measuring device in communication with the catalyst to rise. Baffles or shields may be used in the vicinity of the catalytic sensor element to lessen the amount of heat which is radiated away from that catalytic element either to the reference element, if one is used, or to other surrounding portions of the $NO_x$ sensor assembly.

The $NO_x$ reductant source desirably is a material capable of releasing a reactant which is capable of reducing $NO_x$ on the catalytic surface at the heat flux assembly but not elsewhere. An especially desireable source is cyanuric acid which sublimates into a reductant gas in a suitable temperature range.

The temperature of the catalytic sensor element is obviously converted to an electrically measurable quantity (voltage, resistance, etc.) by the temperature measuring device and is compared to the analogous quantity from the reference element. The difference in temperature is proportional to the $NO_x$ concentration in the measured gas.

The $NO_x$ sensor assembly has an exhaust gas stream containing $NO_x$ drawn or pressured through it. The stream picks up an amount of $NO_x$ reductant from the $NO_x$ reductant source, the $NO_x$ and the $NO_x$ reductant react at the catalytic sensor element to produce a temperature rise at the temperature measuring device, the electrical quantity (voltage, resistance, etc.) is measured and compared to the quantity produced by the reference sensor element, and the gas is then disposed of.

DESCRIPTION OF THE INVENTION

This invention is a self-contained $NO_x$ sensor assembly as shown in FIG. 1 (in block form) comprising an optional filter, a $NO_x$ reductant source, a heat flux sensor assembly comprising a catalytic sensor element capable of detecting $NO_x$ by reacting $NO_x$ with the $NO_x$ reductant and measuring the resulting temperature rise and a reference element capable of measuring the ambient temperature of the gas stream containing both $NO_x$ and $NO_x$ reductant, and some form of flow controller.

Figure 2:
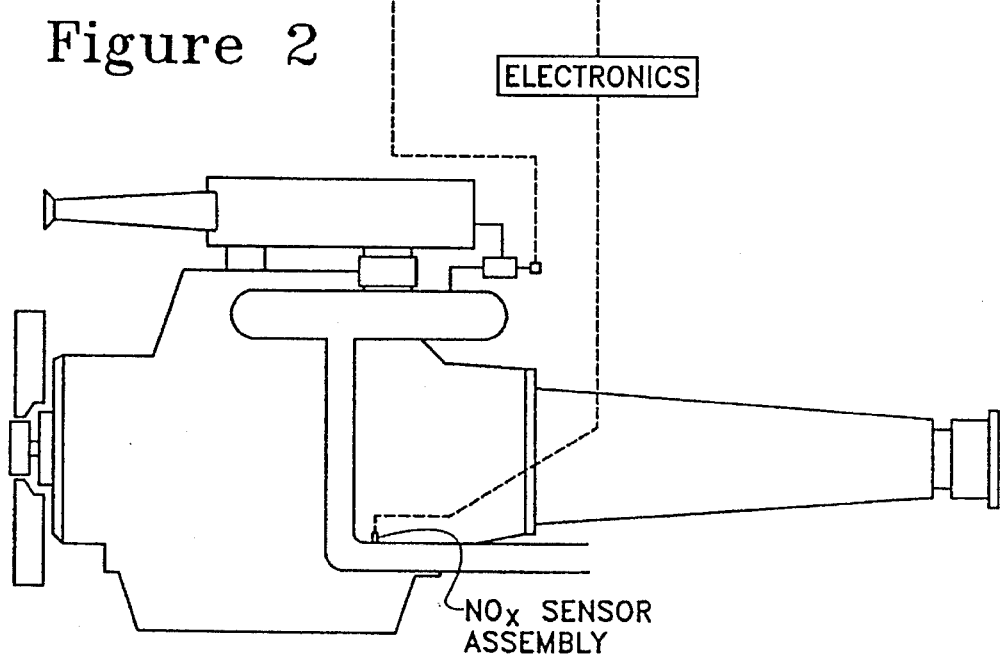
FIG. 2 shows schematically where the inventive device may be used.

Desirably, the self-contained $NO_x$ sensor assembly is of a configuration which is compact, rugged, and uses the temperature of the measured gas to maintain the temperature of the catalytic sensor element at an approximate operating temperature and vaporize or cause sublimation of the $NO_x$ reductant. For instance, as shown in FIG. 2, the $NO_x$ sensor assembly can be mounted in the exhaust line of an internal combustion engine. However, for exhaust gas of a typical vehicular internal combustion engine in which the temperature varies widely depending upon engine speed and load, the temperature of the sensor and the $NO_x$ reductant may be controlled by separate heaters and controllers. The electrical output signals can be fed to an electronics package for determination of $NO_x$ level in the exhaust. That electronic $NO_x$ information could then be sent to a computer controller for an exhaust gas recirculation (EGR) valve. EGR valves, by recirculating exhaust gas to the combustion chambers, lower the amount of $NO_x$ produced by the engine.

Ideally, the $NO_x$ sensor assembly should be fairly small. The amount of exhaust gas passing through the assembly could be in the neighborhood of 1 to 5 cc/minute. Such a sample flow rate permits storage of correspondingly small amounts of reductant within the sensor assembly housing. This also imposes an effective size limitation on the heat flux sensor assembly; both the catalytic sensor element and the reference element, if used, must be of a relatively small size to detect $NO_x$ in such small flowing streams.

One simple embodiment of the inventive self-contained $NO_x$ sensor assembly is found in FIG. 3A. FIGS. 3B through 3E show variants on the section of the $NO_x$ sensor assembly containing an integral $NO_x$ reductant source.

The container (102) for the $NO_x$ sensor assembly may be in the shape shown in FIG. 3A or may be in other convenient shapes, e.g., canisters or shapes conforming to the apparatus into which they fit. As noted above, the inventive device may use the temperature of the combustion gas or exhaust apparatus as the heat source to maintain the temperature at an appropriate operating temperature heat. However, in most instances the sensor will require separate heaters to maintain and control the temperature at an appropriate value. Conformance of the shape to an exhaust manifold or exhaust pipe is acceptable. Container (102) shows a threaded end (104) for mating to the $NO_x$-containing gas source. A similar threaded end (106) is shown at the exit of the inventive device.

The $NO_x$-containing exhaust gases enter through port (108). If the $NO_x$ sensor assembly is to be used with a "dirty" exhaust gas, e.g., one containing particulates such as might be found in a diesel exhaust, optional filter (110) may be incorporated in the $NO_x$ sensor assembly. The filter may not be needed for cleaner burning fuels or combustion sources.

One excellent way of drawing $NO_x$-containing exhaust gases through the self-contained $NO_x$ sensor assembly is by connecting the end of container (102) having exit port (112) to a vacuum source such as the manifold vacuum found in a carbureted or fuel injected Otto cycle engine. This produces a gas flow through the device in the direction of the arrows shown in FIG. 3A. The orifice (114) in baffle (116) may be sized so that it is a critical orifice, that is, the flow through the orifice is at sonic velocity thus producing a constant flow rate of gas to be analyzed through the $NO_x$ sensor assembly independent of small changes in vacuum and partial plugging of particulate filter (110).

After the exhaust gas containing $NO_x$ passes through port (108) and particulate filter (110), it encounters optional restrictor (118). Restrictor (118) may be used to minimize back diffusion of $NO_x$ reductant from $NO_x$ reductant source (120). If desired, the function of restrictor (118) and particulate filter (110) may be combined by choosing, for instance, a fritted metal material having significant flow resistance as the particulate filter (110).

The $NO_x$ reductant source (120) may be in the form of a porous block emanating $NO_x$ reductant. The block may comprise an inert solid, such as carbon or a ceramic, which contains the $NO_x$ reductant or it may be of a material which sublimes or reacts to produce a $NO_x$ reductant. Examples of suitable solid materials include urea, cyanuric acid, ammonium carbonate, etc. The solid reductant may be absorbed on the surface of a fibrous support or in the pores of a porous inert support. It is desirable to have the reductant dispersed on the surface of a high surface area support to maximize the reductant's surface area and promote its vaporization into the gas stream. Additionally, it is desirable to maximize the quantity of reductant in the sensor assembly to provide long life. An optimum surface area and quantity of reductant will take into consideration these opposing objectives. At appropriately low flow rates, the $NO_x$-containing gas will be effectively saturated with the $NO_x$ reductant vapor for passage to the heat flux sensor assembly downstream.

Although not desired because of the bulk required in carrying an amount of $NO_x$ reductant, $NH_3$ may be used as the $NO_x$ reductant by replacing the integral $NO_x$ reductant source (120) with an injector nozzle.

The preferred $NO_x$ reductant is cyanuric acid (a solid) which upon heating decomposes to produce isocyanic acid according to the following reaction:

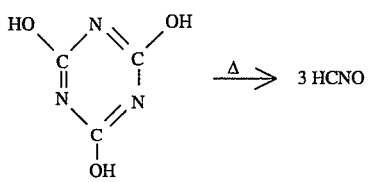

→ 3 HCNO

Isocyanic acid reacts with the various nitrogen oxides (e.g., NO, $NO_2$, etc.) which collectively make up $NO_x$ in a strongly exothermic reaction according to the following illustrative reactions:

$$2NO + 4HNCO + 2O_2 \rightarrow 3N_2 + 4CO_2 + 2H_2O \quad (1)$$

$$2NO_2 + 4HNCO + O_2 \rightarrow 3N_2 + 4CO_2 + 2H_2O \quad (2)$$

Other reactive stoichiometries and, indeed, other reactions are possible to reach the same general result. The above reactions are only examples. The gas stream should contain an excess of $NO_x$ reductant as based on the $NO_x$ present in the gas stream. Said another way, to achieve accurate measurements, the limiting reactant must be the $NO_x$. As a rule of thumb, internal combustion engines contain no more than 500 ppm of $NO_x$ and the reductant must be present at a level in excess of that required to reach with the $NO_x$. For instance, the reactions shown in equation (1) and (2) would require an isocyanic concentration of 1000 ppm for a $NO_x$ concentration of 500 ppm.

Perry, "Rapid Reduction of Nitrogen Oxidizing in Exhaust Gas Stream", *Nature*, December, 1986, Vol. 18/25, has reported that 90% of the NO present in a stream containing 400 ppm is reacted to $N_2$ using cyanuric acid at 325° C. in the presence of a suitable catalyst. When cyanuric acid is chosen as the $NO_x$ reductant source (120), a temperature of about 330° C. is appropriate to achieve the necessary concentration of isocyanic acid. Although placement of the $NO_x$ sensor assembly near the exhaust manifolds (when used with internal or external combustion engines) or near the combustion source in other services (when used with boilers, furnaces, etc.) may be appropriate in some services, auxiliary heating of the $NO_x$ reductant source (120) may be needed (during cold start up) or desired (because of $NO_x$ sensor assembly placement remote from the heat source) such as by heaters (122). The $NO_x$-containing gas also containing $NO_x$ reductant then passes to a heat flux sensor assembly (124). In many services, the temperature of the $NO_x$-containing gas stream as it passes the heat flux sensor assembly (124) is controlled to be different than that of the $NO_x$ sensor source.

Heaters (122) and (126) would usually be electric. We have found that sufficient cyanuric acid is sublimated at above 260° C. to provide an efficiently operable $NO_x$ sensor assembly. The heater (122) for the cyanuric acid $NO_x$ reductant preferably operates at 265° C. to 280° C. The heater (126) for the gas approaching the heat flux sensor assembly (124) desirably operates at a temperature of 280° C. to 340° C., preferably 320° C. to 335° C.

FIGS. 3B through 3E show exemplifying variations of the $NO_x$ reductant source. In FIG. 3B, chunks of a sublimateable $NO_x$ reductant (302) such as cyanuric acid are interspersed in a porous fibrous material (304) such as glass-wool or mineral-wool which is capable of withstanding the temperature of the $NO_x$-containing gas. An optional device for holding the wool in place (306) is shown but may be combined with other functions in the $NO_x$ sensor.

FIG. 3C shows a woven matting (308) containing $NO_x$ reductant followed by optional packing (310) to properly place the matting (308). The packing (310) may be particulate or wool.

FIG. 3D shows a porous monolithic block (312) containing a sublimateable $NO_x$ reductant such as cyanuric acid. The block may be of a porous material such as a glass or fritted metal capable of absorbing $NO_x$ reductant and releasing it upon subsequent use. The block (312) may be followed by a chamber (314).

FIG. 3E shows a variation in which the $NO_x$ reductant source is a series of solid $NO_x$ reductant blocks (320) arranged as baffles in the flow stream. The $NO_x$ reductant sublimes into the gas stream as it flows through the tortuous path formed by the reductant blocks. This structure is excellent in that it maximizes the amount of reductant contained in the $NO_x$ sensor assembly. Fibrous or porous structures (322) may be added as needed to mix the gas stream flowing from the maze formed by the reductant blocks.

Figure 4:
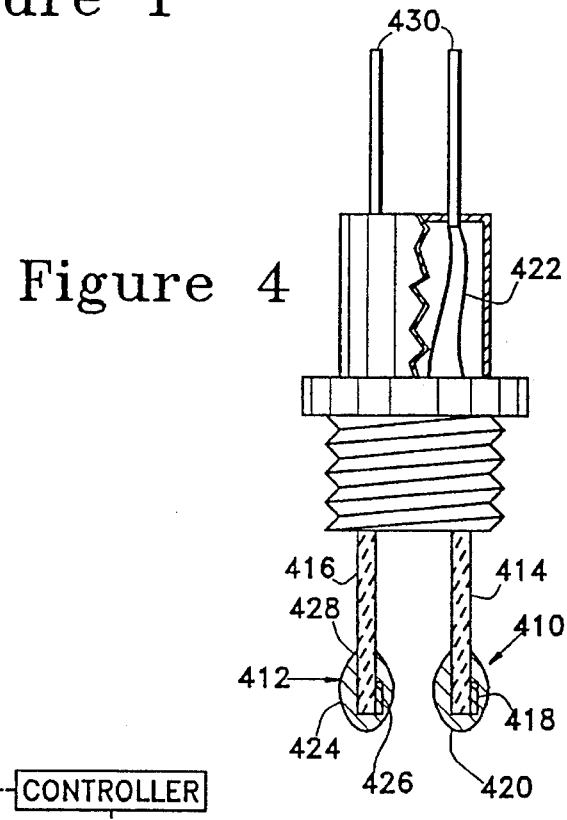
FIG. 4 shows a typical heat flux sensor useful in the inventive device.

The heat flux sensor assembly is made up of two major components which are critical to its operation: the catalytic sensor element and the reference element. First, the catalytic sensor element is made up of a catalyst and a temperature measuring device. FIG. 4 shows a cutaway depiction of a catalytic sensor element (410) and a reference element (412). This variation uses a thermally insulating support or substrate (414 and 416) as portions of the elements. These supports allow the respective elements to be used as probes or fingers extending into the flowing gas stream (as illustrated in FIG. 3A). The substrate should be a thermally-insulating support having sufficient mechanical strength to support the catalyst and temperature measuring devices in the flowing stream. The substrates (414) and (416) may be ceramic or may be a ceramic coating on a metallic support. Suitable ceramic materials include fired kaolin, alumina, silica-alumina, silica, zirconia, or mixtures of these oxides. Ceramic materials which are typically used as catalyst supports are also suitable for the substrate providing that they possess the necessary mechanical strength to withstand the temperature cycling steps as the device is turned on and off, the lengthy times the element will spend at the desired operating temperature, and the normal mechanical shocks endured during installation and operation. These ceramic materials are also suitable because of the variety of procedures available for making the catalytic material (420) adhere to the ceramic substrate (414) and (416).

The temperature measuring device (418) may be any of a variety of devices which produce a variation in a measurable electrical property, e.g., voltage or resistance, as the temperature of the device changes. A bimetallic thermocouple, particularly a chromel-alumel thermocouple, may be cemented to the substrate (414) using known and available ceramic cements. The face of the temperature measuring device away from the support should be substantially free of gas barriers so that the gas to be measured contacts the catalytic surface (420). The temperature measuring device may be a thermistor chosen for appropriate sensitivity in the proper temperature range. If a ceramic substrate (414) is selected, the temperature measuring device need not be discrete and assembled onto the substrate but may instead be made directly on the ceramic surface by known technologies. See, for instance, the procedure for creating thermistors on a ceramic substrate shown in U.S. Pat. No. 4,129,848 to Franc et al. The leads (422) from the temperature measuring device would allow the variable electrical property of the device to be measured. Additionally, the temperature measuring device (418) may be a RTD device which is commercially and widely available and ideal in this service.

Finally, the catalyst layer (420) may be fairly thin to promote conduction of the heat of reaction produced at the surface to the temperature measuring device (418).

The catalyst (420) used in the catalytic sensor element (410) should promote the reaction of $NO_x$ with the $NO_x$ reductant. Although a variety of metals and oxides can catalyze this reaction, many of these catalyze unwanted reactions making the sensor nonspecific for the measurement of $NO_x$. The preferred catalysts are those that catalyze only the reaction of $NO_x$ and the co-reactant such as those described in our co-pending application Ser. No. 07/536,895, filed Jun. 12, 1990. Example catalysts are V, Fe, Mo, W, Mn, Cu, Ni, Co, Cr, Rh, Ru as the metal or oxide in pure form or mixed with or supported on other inert oxides such as $SiO_2$, $Al_2O_3$, $TiO_2$, or mixed oxides such as $SiO_2$-$TiO_2$, $Cr_2O_3$-$Al_2O_3$, zeolites, etc. Preferred catalysts comprised at least one of V, Mo, W oxides and Rh and Ru.

The catalyst layer (420) may be formed by first applying a high temperature oxide layer, such as $TiO_2$, to the temperature measuring device (418). This can be done by known techniques using solutions or colloidal dispersions of the desired oxide followed by heat treating in air or other appropriate gas. Subsequently, the catalyst is applied using a solution of the dried catalytic element in a suitable solvent. Once dipped, sprayed as a wash coat, or otherwise impregnated, the element may be calcined in oxygen or air to produce an active catalyst. Other procedures include vapor disposition, evaporation, and sputtering in an electric discharge or plasma. Reduced platinum group metals such as platinum or palladium, although suitable, may be less desireable at certain higher operating temperature ranges because of their proclivity both for oxidizing residual combustion products such as CO, $H_2$, or hydrocarbons and oxidizing the $NO_x$ reductant with $O_2$.

A particularly suitable procedure for applying the catalyst to the catalytic sensor element is via application of metal salts of the appropriate catalytic metal to the element support. The salt, preferably a sulfate or chloride, is applied as a saturated aqueous solution to maximize the concentration of catalytic metal applied to the element.

Second, the reference element (412) may be similar in design to the catalytic element (410) except that the catalyst layer is excluded and an optional protective layer (424) for the temperature measuring device may be added.

The reference element (412) is intended to provide a comparative temperature measurement which temperature is that of the non-reacted gas flowing past the reference element or catalyst sensor element. The reference element may, in fact, be an arbitrarily selected fixed value element if the temperature of the gas and the environment "seen" by the catalytic sensor element can be carefully controlled. For instance, if the catalytic sensor element is placed in an iso-thermal environment such that the surrounding temperature is controlled rather than measured, a precision resistor (if the temperature measuring device for the catalytic sensor element is a RTD or a thermistor) or a voltage source (if the temperature measuring device is a thermocouple) may be used instead of a reference element which measures local temperature.

Neither element is directly heated using, for instance, resistance heating.

In FIG. 4 the reference element (412) may be made up of a mechanical support, a temperature measuring device, and an optional protective layer. The variation shown in FIG. 4 includes a mechanical support (416) similar in function to support (414). The temperature measuring device (426) is mounted on the support or, as with the catalytic element, may be produced integrally with the ceramic surface of the support if, of course, the support is ceramic. The protective coating (428) is optional depending upon the corrosivity of the gas stream measured and the reactivity of the temperature measuring device employed.

The optional protective coating (428) on the reference element may be of alumina, silica, epoxy polymer, carbon, or other heat conducting material. The coating is to protect the temperature measuring device (426) from corrosive elements, e.g., $SO_2$, $H_2O$, $NO_x$, etc., in the gas stream but not to interfere in the reference element's task of measuring local temperature. Additionally, the protective coating (428) improves the match of the thermal mass of the reference element (418) and the catalytic sensor element (410). If the catalytic sensor element (410) were to be coated and the reference element were not, the thermal mass of the surface element would be much less and would respond to changes in ambient temperature much more quickly than the catalytic sensor element. Such a response difference clearly could cause errors in the $NO_x$ measurements. Further, the protective coating (428) provides cross-sectional and surface areas of the reference element (410) relatively similar to those of the catalytic sensor element (412). Similarity in those areas also results in similar convective heat transfer loads.

The reference element (410) desirably is designed so that the configuration of the gas as it flows past is similar to the flow past the catalytic sensor element (412). Said another way, the aerodynamic shapes of the two elements should be similar. The two elements ideally should be placed in similar and representative flow regions in the measured gas, i.e., both should be placed in a turbulent flow region of the gas so that the gas measured is representative. Placement of one element in a boundary layer and another in a turbulent flow region should be avoided.

The two elements should be optimized in shape and materials of construction to minimize heat loss via conduction or radiation. Support materials should be selected so that the heat of reaction on the catalytic coating (420) of the catalyst sensor element (410) is maintained at the temperature measuring device (418). The elements should be as small as is practically possible to permit quick resolution of temperature and $NO_x$ contact. Use of small elements also results generally in less radiation heat loss to the surroundings. The two elements should have similar thermal mass. The catalytic sensor and reference elements need not be in the configuration shown in FIG. 4.

The signals emanating from each of the temperature measuring devices in the catalyst sensor element and the reference element are compared using well-known circuitry (wheatstone bridges, differential amplifiers, etc.) and the $NO_x$ content of the gas stream measured via calibration. Because of the linearity of the inventive assembly, the $NO_x$ concentration may be measured directly after such calibration through the tabs (430).

This invention has been disclosed both by description and by illustration. The illustrations are only examples and should not be used to limit the claimed invention in any way. Additionally, it will be apparent to a reader having ordinary skill in this art that other variations and equivalents will operate in the same way in measuring $NO_x$ and yet be within the spirit of these claims.

We claim as our invention:

1. A self-contained device for measuring $NO_x$ concentration in a flowing gas stream comprising:
   a. a container adapted to receive a flowing gas stream containing $NO_x$;
   b. a $NO_x$ reductant source situated within the container and adapted to introduce a $NO_x$ reductant into the flowing gas stream containing $NO_x$;

c. a heater capable of heating the $NO_x$ reductant source to a temperature above 260° C. thereby releasing $NO_x$ reductant into the flowing gas stream containing $NO_x$; and d. a heat flux sensor assembly situated within the container wherein the heat flux sensor assembly comprises a catalytic sensor element and a reference element, said catalytic sensor element comprising a catalyst coated on the periphery of a temperature sensing device whereby the catalytic sensor element catalytically reduces the $NO_x$ with the $NO_x$ reductant and measures the temperature rise from the reduction.

2. The device of claim 1 additionally comprising a heater for heating the flowing gas containing $NO_x$ prior to its passage over the heat flux sensor assembly.

3. The device of claim 1 where the $NO_x$ reductant source comprises porous cyanuric acid.

4. The device of claim 3 additionally comprising a filter for removing particulates from gas containing $NO_x$ before the $NO_x$ reductant is introduced into the flowing gas containing $NO_x$.

5. The device of claim 1 where the $NO_x$ reductant source additionally comprises a woven material.

6. The device of claim 5 additionally comprising a filter for removing particulates from gas containing $NO_x$ before the $NO_x$ reductant is introduced into the flowing gas containing $NO_x$.

7. The device of claim 1 where the $NO_x$ reductant source additionally comprises glass or mineral wool.

8. The device of claim 7 additionally comprising a filter for removing particulates from gas containing $NO_x$ before the $NO_x$ reductant is introduced into the flowing gas containing $NO_x$.

9. The device of claim 1 where the $NO_x$ reductant source additionally comprises a monolith.

10. The device of claim 9 additionally comprising a filter for removing particulates from gas containing $NO_x$ before the $NO_x$ reductant is introduced into the flowing gas containing $NO_x$.

11. The device of claim 1 where the $NO_x$ reductant source comprises a labyrinth.

12. The device of claim 11 additionally comprising a filter for removing particulates from gas containing $NO_x$ before the $NO_x$ reductant is introduced into the flowing gas containing $NO_x$.

13. The device of claim 1, additionally comprising a filter for removing particulates from gas containing $NO_x$ before the $NO_x$ reductant is introduced into the flowing gas containing $NO_x$.

14. The device of claim 13 additionally comprising a flow controller situated within the container and adapted for controlling the flow of flowing gas containing $NO_x$ through the container.

15. The device of claim 13 additionally comprising a restrictor adapted to mix $NO_x$ reductant into the flowing gas containing $NO_x$.

16. The device of claim 1 where the catalytic sensor element comprises a temperature sensing device selected from a thermocouple, RTD, and thermistor.

17. The device of claim 16 where the catalytic sensor element comprises a catalyst containing a metal or metal oxide of V, Fe, Mo, W, Mn, Cu, Ni, Co, Cr, Rh, or Ru or mixtures.

18. The device of claim 17 where the catalytic element comprises a catalyst containing V, Mo, W oxides; or Rh or Ru.

* * * * *